United States Patent [19]

Thomas

[11] 4,136,170

[45] Jan. 23, 1979

[54] METHOD OF EXTRACTING A HYPERGLYCEMIC FACTOR

[76] Inventor: André Thomas, 8, Rue Pierre et Marie Curie, 75005 Paris, France

[21] Appl. No.: 742,908

[22] Filed: Nov. 18, 1976

[30] Foreign Application Priority Data

Nov. 21, 1975 [FR] France ............................. 75 35645
Nov. 21, 1975 [FR] France ............................. 75 35646
Nov. 10, 1976 [FR] France ............................. 76 33847

[51] Int. Cl.² ......................................... A61K 35/28
[52] U.S. Cl. ................................................ 424/95
[58] Field of Search ........................................ 424/95

[56] References Cited

U.S. PATENT DOCUMENTS 2,091,730   8/1937   Fenger ................................. 424/95

*Primary Examiner*—Sam Rosen
*Attorney, Agent, or Firm*—Ostrolenk, Faber, Gerb & Soffen

[57] ABSTRACT

A hyperglycemic factor causes general glycosuric expulsion is prepared by extracting said factor from red bone marrow obtained from flat bones from which the hard bony walls have been removed.

17 Claims, No Drawings

METHOD OF EXTRACTING A HYPERGLYCEMIC FACTOR

This invention concerns a method of extracting a hyperglycemic factor from red bone marrow and/or physiologically similar organs; it is also related to the novel extract obtained by this method, and its pharmaceutical applications.

Red bone marrow comes from flat bones, for example from slaughtered animals. These bones are suitably prepared and kept at low temperature for a short period, or stored after freezing. They are sawn to pieces, and the hard outer bony walls are removed. The red marrow with its spongy bony matrix is then cut into small pieces and crushed. The resulting pulp undergoes grinding and extraction processes.

This novel method eliminates from extraction any undesirable substances originating in the spongy bony matrix containing the red marrow cells. These substances include not only salts, but also organic matter such a gelatine, osseo-mucoids or osseo-albumen.

This new method consists of grinding the pulp of red bone marrow and spongy bony matrix in the presence of cold distilled water, removing bony particles by filtration; subjecting the filtrate to extraction in a neutralized medium, at temperatures of between 60 and 100° C, then carrying out further filtration, concentration and intensive purifications of the extract.

In one embodiment of the invention, extraction is done, not on the actual untreated ground material, but on an acetonic powder of red bone marrow. This powder is prepared by grinding the crushed red marrow directly at high speed in pure acetone (e.g. 1 kg red marrow pulp to 5 liters acetone), repeating the operation at least twice; the ground material is then strained to separate out residual bony particles, and finally dried. The resulting acetonic powder can be stored at low temperature. This acetone treatment largely eliminates undesirable acetosoluble substances, removing about 40% or more. Actual extraction is then performed on the acetonic powder.

The invention comprises a number of alternative forms of extraction.

Where the ground pulp is treated with cold distilled water, the procedure is as follows : half the distilled water needed to reach the final specified dilution is added to the pulp comprising red bone marrow and spongy matrix from flat bones. Intensive grinding is done in this distilled water, using a high-speed grinder, such as a Polytron. The cold distilled water lyses the cells. The liquid is filtered to remove all bony particles in suspension (filtrate$_1$). This filtrate is then transformed into a buffer system.

In one embodiment of the invention, pH levels of approximately 7.5 are used. This is obtained by adding a volume equal to the volume of filtrate$_1$ of a double-concentration buffer, in order to adjust the pH to about 7.5; a buffer solution of the sodium phosphate type, with a concentration of 0.2 M or any other standard biological buffer, can be used. This new filtrate $_{1+t}$ is then extracted, by heating the neutralized solution to between 60 and 100° C for a period depending on the amount treated, generally between 30 minutes and 3 hours. In another embodiment of the invention, pH levels of between 4 and 7, and preferably around 4.5, are used. Buffers using strong or organic acids can be used, or any other existing biological acid buffer. This acid pH produces salt-free media, as in the case where extraction is performed in a basic medium.

In either case (alkaline or acid pH), extraction can be completed by adding a low concentration of alcohol (for example 5% final concentration) to the mixture.

When filtrate$_1$ has been prepared, it is heated to between 60 and 100° C for a period depending on the amount treated, generally between 30 minutes and 2 hours. After cooling, this ground product is filtered, producing filtrate$_2$. A fine, dark brown pulpy residue without bony particles remains on the filter; filtrate$_2$ is pale yellow, almost limpid, and it contains only heat-resistant substances from the red bone marrow, heat-sensitive products having been eliminated.

This filtrate$_2$ is then strongly concentrated, for example with a rotary vacuum concentrator or any other suitable apparatus. It may be concentrated between 5 and 20 times. This produces the concentrated raw extract.

This concentrated raw extract can be dialysed at this stage against deionized water, or subjected to ultrafiltration or electro-dialysis; when extraction is performed with an acid pH, the extract contains very little salt, and these operations are not necessary, since subsequent purification operations are to be carried out.

The concentrated raw extract then undergoes preliminary purification to remove substances which will not be active for the application envisaged. This is done by submitting the extract to ultrafiltration, for example on an Amicon diaphragm, for a molecular weight of 10,000, it is concentrated and left to precipitate at +4° C. The ultrafiltrate then contains only heat-resistant substance with a molecular weight of not more than 10,000. Preliminary purification of the raw extract can also be provided by precipitation. This is done with alcohol having a alcohol concentration of approximately 35%, finally, for a short period, such as 1 to 2 hours at 4° C; the mixture is then centrifuged and the alcohol removed by concentration-distillation. The concentration crude extract can also be heated in a boiling water-bath for a few minutes, then centrifuged: although the extract has been prepared at high temperature, its concentrate can still precipitate at temperatures of around 98 to 100° C. In all cases, ultrafiltrates and surface layers are yellow, and show intense yellow-green fluorescence in ultra-violet light. Although they contain relatively small amounts of salt, extracts can be dialysed against deionized water at +4° C. The concentrated raw extract can also undergo electrodialysis.

Partly purified supernatent substances, and ultrafiltrates and dialysates undergo chromatography and are then fractionated by gel-filtration; this is done by existing methods on a suitable gel. The percentage fractionation transmission curves show peaks which are separated. Initial or head peaks, 1, 2, 3, depending on mass conditions, show low or no fluorescence. In particular, they contain peak 1, the active substance being sought. Then comes a large peak, for example peak 4, containing substances which are intensely fluorescent in ultra-violet light, but not the product sought in the present case. Active fractions are re-concentrated and repurified by successive fractionating operations. They are used in solution, or dried and made into powder by known processes.

In the recommended embodiment of this invention, extraction is performed on acetonic powder. Such extraction can be carried out under the conditions mentioned above, either with a saline buffer or with a hydroalcoholic solution, which can be neutralized by the acetonic powder itself.

In the event of buffer extraction, various biological saline buffers can be used, within the limits already mentioned.

A phosphate buffer is chosen as one of the simplest. An 0.1M concentration at pH 6.8, obtained by mixing 0.05M disodic phosphate and 0.05M monopotassic phosphate, may be adopted. Although the invention is not restricted to this, the ratio can be 1 kg acetonic powder to 5 to 10 liters buffer. Extraction is performed at between 60 and 98° C, for example at 65° C, for 1 to several hours, with agitation. The extract is then cooled and decanted.

A simple, efficient method for treating large quantities is to precipitate directly the phosphates that have not yet been precipitated by the calcium released by bony residues, using calcium chloride, molecule per molecule, in the form of brushite. The pH is readjusted to 6.8 and the mixture is agitated at +4° C for an adequate period, of from a few hours to 1 day, for example. Experience has shown that adsorption by brushite clarifies the extract, without it being necessary reprecipitate it at this stage by pH variation or any other method, which could be more or less inconvenient. Furthermore, brushite does not adsorb the active product in extract, because eluates of brushite precipitates have no hyperglycemic activity after adsorption : on the contrary, they may be hypoglycemic, thereby removing undesirable or even inhibiting substances from the extract. The extract is then centrifuged or filtered, and concentrated approximately 20 times, for example, in a vacuum, using a rotary concentrator, for example. This centrifuged concentrate corresponds to the raw extract, still containing large amounts of salts and various proteolipidic and glucidic substances. It can then be semi-purified, by precipitation at low temperature in various ways, using ethanol, methanol or a salt such as zinc acetate: the extract will be plentifully precipitated by very low concentrations of zinc acetate, 0.004M or less; the small amount of zinc added will have no toxic effect in the final preparation, which results from the supernatent layer and not the precipitate; on the contrary, it reinforces hyperglycemic properties. Precipitation can also be performed using other substances or mixtures. The extract is the centrifuged and the supernatent substance is removed and possibly dried; in this case it can be redissolved in various concentrations of ethanol, which helps to reduce salt content further.

An alternative embodiment of the process is to carry out semi-purification after ultrafiltration of the extract. Precipitation operations are then the same as those described above, but they involve an ultrafiltrate which is already partly purified.

For intensive purification, dialysis, electrodialysis, ultrafiltration or inverse osmosis may be used, or chromatographic fractionation by gel-filtration, using existing methods, and as described earlier. The active extract is then dried by lyophilization or dessication under vacuum.

A second type of extraction, also within the scope of this invention, is to use the acetonic powder of red bone marrow with hydroalcoholic solutions of 5% and above, for example an 80° alcoholic solution; in this case the proteolipidic acetonic powder produces its own buffer effect within pH limits indicated, and the pH can even be adjusted if necessary to around 6.8; hydroalcoholic extraction, for example in ratios of 1 kg powder to 5 to 10 liters hydroalcoholic solution, is performed in the same conditions as extraction by phosphate buffer such as described above; in this case, however, the concentration must allow for elimination of alcohol by distillation. The residual aqueous phase is then treated as described above for extraction with a saline buffer. In the case of hydroalcoholic extraction, however, as with other buffers such as acetate, and since no buffer containing phosphate is used at the start, clarification is performed by adding ready-prepared, fresh, washed brushite (calcium phosphate precipitate adjusted to a pH level of 6.8 and centrifuged). Any other effective adsorbent producing a similar effect to brushite can of course be used in the case of initial extraction with a hydroalcoholic solution or other buffers than phosphate.

However, an important point included in the invention is that, if the active product is not adsorbed on a mineral adsorbent such as brushite, this can be done very effectively on organic, lipoproteic precipitates produced by the extract itself. This involves cryoprecipitation extraction.

The semi-purified extract, preferably after phosphate extraction, is then frozen in transparent, flexible plastic tubes, for example to −25° C. This produces cryoprecipitation in the form of fine grains, a small amount of which collects on the surface, while the major part collects at the bottom of the tubes, and which selectively adsorb the active compound and concentrate it.

When these active grains are thawed at atmospheric temperature, they correspond to thawing heads, in other words to the fraction corresponding to the lowest freezing point. These heads are highly concentrated, and are collected as soon as they thaw, partly on the surface but mainly at the bottom of the tubes, by cutting into these, for example. Remaining cryoprecipitates, which will thaw later and which are increasingly aqueous, do not adsorb the active substance at a sufficient concentration. These thawing heads are centrifuged and the active substance, which is hydrosoluble, is separated by simple selection of adsorbent lipoproteic precipitates, which are themselves inactive.

Other methods of adsorption, using organic structures, can be used. For example, the extract can be treated with ethyl ether to produce an interface precipitate which adsorbs the active compound. Alternatively, the extract can be precipitated with zinc acetate in the presence of calcium, to produce very regular coacervates which also adsorb the active product selectively, and concentrate it.

The various extraction methods apply to any organ which, like red bone marrow, can release a hyperglycemic compound.

Extract and products obtained in this way are used as a therapeutic agents which can be administered intravenously or parenterally.

They possess characteristic physiological properties, containing a factor which, when injected into the blood, causes an extraordinarily high rise for several hours in the glucose level of circulating blood, together with urinary expulsion of this glucose, which thus accumulates in the bladder.

Figures of rabbits, for example, can show gradual glycemia reaching 10.5g per liter blood serum in 5 hours, or exceeding this. In addition, urinary glucose expulsion raises glucosuria to experimental levels of more than 50g per liter urine; in certain cases glucosuria can even reach 100 g per liter.

Detailed biochemical investigation shows that, contrary to existing hyperglycemic hormones, this glucose, released in such massive quantities, is not only the result of degradation of glycogen or glycogenolysis in certain organs like the liver, but is general. For example, contrary to glucagon which has no effect on glycogenolysis in muscles, this new factor reduces the rate of glycogen in muscles and main organs, even going so far as to eliminate it entirely. This general glycogenolysis and releasing of glucose into the blood from other sources builds up the considerable glycosuric expulsion referred to.

The hyperglycemic factor, separated by this new process, does not alter blood and cardiac functions, as is revealed by measurements and electrocardiograms. In fact, at physiological doses it has a beneficial effect on such functions. Organs are not affected and the blood glucose rate subsequently returns to normal. This factor possesses heat-stability and is proteinic; it produces a sharp reaction with p.dimethylaminobenzaldehyde according to Ehrlich, which indicates the presence of glycoprotein. This test is confirmed by the specific Elson-Morgan reaction.

Without any departure from the invention, the preparation principles described can be applied to any organ physiologically equivalent to red bone marrow.

The invention is illustrated by, without being confined to, the following examples.

EXAMPLE 1

Preparation of red bone marrow extract — treatment with cold distilled water.

Bony pelvic girdles of calves are removed immediately after slaughtering. Muscles are removed and the bones are stored at low temperature, preferably deep-frozen. The bones are then sawn into pieces and their outside hard bony walls roughly removed. The red bone narrow is cut into small pieces and treated either immediately or after storage at −80° C for several months. These pieces are crushed and the resulting pulp placed in cold distilled water. If the final proportion is to be 1 kg red marrow pulp to 10 liters, 5 liters of distilled water can be added, in other words half the final volume, or else the total volume of 10 liters can be added at the beginning.

The suspension is ground intensively in a high-speed grinder, for example a Polytron, for a sufficient period, namely 4 times 5 minutes. The ground material is filtered on a thick layer of gauze, or any other screen capable of retaining all bony particles in the red marrow matrix, suspended in the ground material.

(a) Extraction in an alkaline medium.

The volume of filtrate obtained is then doubled with an 0.2M phosphate buffer at pH 7.5, containing a quantity of 10% alcohol. This produces 1 kg ground product in 10 liters 0.1 M buffer at pH 7.5 with an alcohol concentration of 5%. This preparation is heated in a water-bath to 60° C for 30 minutes. It is allowed to cool and then filtered. The filtrate, which is almost limpid and pale yellow in colour, is concentrated approximately 10 times in a rotary vacuum concentrator. It is ultrafiltered on a diaphragm for a molecular weight of 10,000, precipitated, fractionated by gel-filtration using Sephadex G 50 Fine gel. Fractions corresponding to head peaks, mainly peak $_1$, are collected and their protein content measured. Intensive purification is continued by successive fractionations. They are used either in a solution adjusted to a known protein content, or turned into powder, which is soluble in distilled water, and limpid in a concentrated solution, at approximately pH 6.

(b) Extraction in an acid medium

The volume of filtrate is doubled with an 0.2M acetate buffer with pH 4.3, which may contain a quantity of 10% alcohol. This produces 1 kg ground product in approximately 10 liters 0.1M buffer at pH 4.3, possibly containing 5% alcohol. If the total amount of distilled water is used at the start to prepare the suspension and for grinding of the red marrow, components of the acid buffer, namely acetic acid, are added after grinding and removal of bony fragments until the pH level stabilizes at 4.3.

The preparation is then heated in a water-bath to 60° C for 30 minutes, or in a boiling water-bath for 30 minutes. It is allowed to cool, then filtered. The filtrate is limpid and pale yellow in colour. It is concentrated in a rotary vacuum concentrator. If concentration is sufficiently intensive (20 times or more), the concentrate will begin to precipitate when warm; precipitation is allowed to be terminated at +4° C, and the resulting product is filtered or centrifuged. Precipitation of substances not required for the specific application is completed by precipitation with alcohol, by adding 70% alcohol, volume per volume, which raises the alcoholic level to approximately 35% for 1 or 2 hours, at +4° C, and this centrifuged. It is also possible to heat the filtrate in a boiling water-bath for 5 minutes, and centrifuge after cooling.

These preparations are subjected to fractionation by gel-filtration, using Sephadex G 50 Fine, balanced by 0.02M acetate buffer at pH 4.3. Only head peaks$_{1,2}$and$_3$ are removed; they are concentrated 5 times, and their protein content is measured; purification of this extract continues by successive fractionations. It is dessicated and powdered. This powder is soluble in distilled water; with slight acidification, the solution, even concentrated, remains perfectly limpid and colourless. It can be resterilized. The extract can also be subjected to other concentration methods, ultrafiltration, electrodialysis.

EXAMPLE 2

Extraction of the hyperglycemic compound from a saline buffer.

Red bone marrow separated from the hard bony walls of flat bones of young slaughtered animals, as described in example 1, is frozen at a low temperature. It is crushed, then ground very finely two or three times in a high-speed grinder in pure acetone, at the rate of 1 kg red marrow pulp to 5 liters acetone. The acetonic ground matter is decanted, strained on a screen to remove residual bony particles, and collected on a Buchner filter. The resulting acetonic pulp is dried to produce the acetonic powder required for extraction. It can be kept in this condition at low temperature. This preliminary acetonic extraction removes around 40% or more acetosoluble substances.

Extraction of the pulp is performed by a saline buffer at high temperature. A sodium phosphate buffer at a concentration of 0.1M, and with a pH level of 6.8, is recommended, to be used at the rate of 1 kg acetonic powder to 5 liters buffer. Extraction is performed at 65° C for 1 hour, under uninterrupted agitation. The cooled and decanted extract is precipitated with calcium chloride, molecule per molecule, in relation to the buffer phosphate. After readjustment of the pH to 6.8, precipitation-adsorption by the calcium phosphate (brushite)

thus formed in the extract itself continues at +4° C for 10 hours. The brushite does not adsorb the hyperlycemic compound, but separates out inactive and inhibiting fractions by adsorption. The extract is then centrifuged or filtered, and concentrated 20 times under vacuum.

The resulting raw extract then undergoes semi-purification by precipitation at +4° C for from a few hours to a day, using ethanol or methanol, or very small amounts of zinc acetate with a final concentration of not more than 0.004M. Centrifuging is used to separate the supernatent substances containing the active product, which is dried and re-extracted, or else ultrafiltered and used in that form or precipitated.

Intensive purification of the extract is done by various existing methods of dialysis and biochemical fractional distillation. The extract is dried by lyophilization or dessication under vacuum.

EXAMPLE 3

Extraction of the hyperglycemic compound by a hydroalcoholic solution.

The acetonic powder of red bone marrow is extracted with 80% alcohol at the rate of 1 kg powder to 5 liters alcohol, and with a pH lever adjusted to 6.8. Extraction continues at 65° C for 1 hour, under uninterrupted agitation. The cooled extract is decanted and filtered, then concentrated 20 times in a vacuum, in order to distill off the alcohol. A precipitate paste of freshly prepared, washed brushite is added to the remaining aqueous phase, pH being adjusted to 6.8. Adsorption continues at +4° C for 10 hours, under uninterrupted agitation. The extract is then centrifuged and semi-purified by precipitation, or purified by fractionation as described in Example 1.

EXAMPLE 4

Separation of the hyperglycemic compound by cryoprecipitation.

The crude or semi-purified extract resulting from the process described in Example 1 or in Example 2, but preferably after extraction with a saline buffer, and possibly after ultrafiltration, is frozen to −25° C in flexible plastic tubes.

This causes cryoprecipitation in the form of fine grains, some of which collect on the surface, but most of which are to be found at the bottom of the tubes; these correspond to lowest freezing point fractions, and are the most concentrated. They selectively adsorb hyperglycemic compound, and thaw first, at atmospheric temperature, constituting thawing heads which are removed as soon as they thaw. They are then centrifugalized. The centrifuging residue is eluted in an aqueous solution and used in this form, or purified as described in Examples 1 and 2. The remaining proteolipidic button is inactive.

EXAMPLE 5

Pharmacological properties.

The new extract is injected into the blood of normal male or female rabbits weighing approximately 4 kg. Their rate of glycemia and glycosuria is measured over the next few hours. Similarly, corresponding rates of glycogen and glucose are measured in their main viscora and muscles. Results reveal that the hyperglycemic compound of red bone marrow quickly produces glycogenolysis, mainly in liver and organs, but also in muscles, contrary to the effect of glucagon. The resulting glucose reaches very high rates both in blood and urine. Glycemia and glycosuria increase correlatively, resulting in very intense glycosuric expulsion, even in rabbits which are already hyperglycemic and, more remarkable, in a diabetic rabbit with intense glysuria, without any significant increase in glucemia. The hyperglycemic compound of red bone marrow enters into the very complex physio-pathological cycle of hormonal regulation of glucids.

The following figures are given as examples.

After extraction as described in Example 2, the dose injected into the rabbit, expressed in proteins, is 210 γ/kg, raising glycemia from 0.182g % to 0.416g % in ½ hour, and glycosuria to 7.17g % in 5 hours. This dose can even be reduced to 140 γkg, raising glycemia to 0.59g % and glucosuria to 5.48g % in 5 hours. For larger doses, glycemia can reach the very high rate of 1.03g % in 5 hours, and glycosuria 4.81g %. Glycosuria sometimes reaches a figure of 8.69g % and even, in the case of the cryoprecipitation method described in Example 3 and after extraction with a phosphorus buffer, 9.95g %.

After precipitation with zinc acetate, the glycemia rate can rise extremely fast, reaching 0.615g % in only one hour, while after the same period the glucose rate in urine is already 3.38g %.

Similarily, after extraction as described in Example 3, the injected dose can be less than 100 γ/kg, producing 0.673g % glycemia and 0.522g % glycosuria in 1 hour. The lyophilisate and dialysate also provide significant results: at a protein dose of 450 γ/kg, for example, the dialysate produces 6.24g % glycosuria in 5 hours.

In a rabbit which is already hyperglycemic, the extract described in Example 1 causes only a fairly slight increase in glycemia, from 0.338g % at the start to a maximum of 0.437g % in 1½ hour, but the curve then decreases gradually, dropping to point 0.342g % in 5 hours; at this stage, on the other hand, glycemia reaches 7g %.

Finally, in the diabetic rabbit, after extraction as described in Example 2, glycemia starts from a high rate of 0.7g %, reaching a maximum of only 0.966g % in ½ hour, then decreasing to 0.568g % in 5 hours; at this point glycosuria is 5.28g %, showing that excess glucose is flushed out in the urine.

The hyperglycemic compound also has other pharmacological properties: it acts on lipid catabolism, reduces the cholesterol rate from 0.131g % to 0.106g % in serum in only 5 hours and after a single injection. Current experiments suggest that it can affect cell growth. It has no harmful effect on the functioning of the heart, as is shown by electrocardiograms.

What is claimed is:

1. A process for preparing a hyperglycemic factor, causing general glycosuric expulsion, characterized by extracting said factor from red bone marrow obtained from flat bones from which the hard bony walls have been removed by contact thereof with an aqueous medium at 60–100° C and at a buffered pH of between 4 and 7 or of approximately 7.5 for a time sufficient to extract said factor.

2. A process as defined in claim 1, in which the extraction is preceded by treating with cold water the pulp resulting from grinding of the marrow and its bony matrix, to produce a filtrate which is extracted.

3. A process as defined in claim 2, in which extraction is performed a buffered alkaline pH of approximately 7.5.

4. A process as defined in claim 2, in which extraction is performed with a buffered acid pH of between 4 and 6.9.

5. A process as defined in claim 2, in which a low-concentration of alcohol is added to the medium.

6. A process as defined in claim 1, in which extraction is performed on acetonic powder obtained by grinding the red bone marrow at high speed in pure acetone, repeating the operation at least twice, and collecting the resulting acetonic powder.

7. A process as defined in claim 6, in which extraction of the acetonic powder is performed by an 0.1M phosphate buffer with a pH of 6.8.

8. A process as defined in claim 7, in which calcium chloride is added, molecule for molecule, in order to precipitate phosphates in the form of calcium phosphate (brushite).

9. A process as defined in claim 6, in which the extract is purified by precipitation in ethanol, methanol, zinc acetate or methylal-methanol mixtures, to produce a supernatent layer containing a high concentration of the required compound.

10. A process as defined in claim 6, in which extraction of the acetonic powder is carried out using a hydro-alcoholic solution containing 5 to 80% alcohol, the acetonic powder itself being used as buffer.

11. A process in which the extract obtained as defined in claim 10 is purified by cryoprecipitation, the active product being concentrated in thawing heads.

12. A hyperglycemic factor extract obtained using the process defined in claim 1 of red bone marrow obtained from flat bones.

13. A process as defined in claim 6, in which extraction is performed in a buffered medium having an alkaline pH of approximately 7.5.

14. A process as defined in claim 6, in which extraction is performed in a buffered medium having an acid pH of between 4 and 6.9.

15. A process as defined in claim 6 in which a low concentration of alcohol is added to the neutralized medium.

16. A process in which the extract as defined in claim 2 is purified by cryoprecipitation, the active product being concentrated in thawing heads.

17. A hyperglycemic factor causing general glycogenolysis and glycosuric expulsion, comprising an extract of a red bone marrow obtained from flat bones and having the characteristics of being heat-stable, proteinic, exhibiting low or no fluorescence in ultraviolet light and sharply reacting with p. dimethylaminobenzaldehyde.

* * * * *